United States Patent [19]

Chow

[11] 4,438,135
[45] Mar. 20, 1984

[54] 1-(3,4-BIS-(3-(LOWER ALKOXYCARBONYL)-2-THIOUREIDO)-PHENYL-1-PHENYLTHYLENES

[75] Inventor: Alfred W. Chow, Radnor, Pa.

[73] Assignee: SmithKline Beckman Corporation, Philadelphia, Pa.

[21] Appl. No.: 456,199

[22] Filed: Jan. 7, 1983

[51] Int. Cl.$^3$ .................. C07C 157/12; A61K 31/325
[52] U.S. Cl. ....................................... 424/300; 560/16
[58] Field of Search ........................... 560/16; 424/300

[56] References Cited

U.S. PATENT DOCUMENTS

| | | | |
|---|---|---|---|
| 3,657,267 | 4/1972 | Van Gelder et al. | 260/309.2 |
| 3,856,847 | 12/1974 | Kohmoto | 560/16 |
| 3,961,063 | 6/1976 | Parish | 424/263 |
| 4,002,761 | 1/1977 | Parish | 424/263 |
| 4,020,095 | 4/1977 | Noguchi | 424/300 |
| 4,029,813 | 6/1977 | Noguchi | 424/300 |

OTHER PUBLICATIONS

Derwent Abstract No. 55442V/31.

*Primary Examiner*—Michael L. Shippen
*Attorney, Agent, or Firm*—William H. Edgerton; Richard D. Foggio; Alan D. Lourie

[57] ABSTRACT

1-(3,4-bis-(3-lower alkoxycarbonyl)-2-thioureido)-phenyl)-1-phenylethylenes, which have anthelmintic activity, are prepared by reacting various 1-(3,4-diaminophenyl)-1-phenylethylenes with an alkoxycarbonylisothiocyanate which is prepared, in turn, from an alkali metal thiocyanate and a lower alkyl haloformate.

11 Claims, No Drawings

1-(3,4-BIS-(3-(LOWER ALKOXYCARBONYL)-2-THIOUREIDO)-PHENYL-1-PHENYLTHYLENES

This invention relates to 1,1-diphenylethylene anthelmintic compounds whose structures are distinguished by having one of the phenyl rings substituted by two adjacent lower alkoxycarbonylthioureido groups. The compounds have anthelmintic activity against nematodes, cestodes and flukes.

BACKGROUND OF THE INVENTION

A series of 5-acyl benzimidazoles which have a carbamyl substituent at the 2-position are described as anthelmintic agents, U.S. Pat. No. 3,657,267. The marketed species of this group is mebendazole which is methyl (5-benzoyl-1H-benzimidazol-2-yl)carbamate.

German patent application DT 2303048 (Derwent No. 55442/31) discloses certain anthelmintic benzophenone structures which have a bis acylamino substitution pattern. U.S. Pat. Nos. 3,961,063 and 4,002,761 describe anthelmintic compounds whose structures have a pyridine ring substituted by both a benzophenone, among others, and two bisacylamino groups. None of this art suggests the preparation of the 1,1-diphenylethylene compounds of this invention.

DESCRIPTION OF THE INVENTION

This invention relates to 1-(3,4-bis-(3-lower alkoxycarbonyl)-2-thioureido)phenyl)-1-phenylethylenes which have anthelmintic activity. These compounds have a low chemical cost which is advantageous in this field.

More specifically, the compounds of this invention are illustrated by the structural formula:

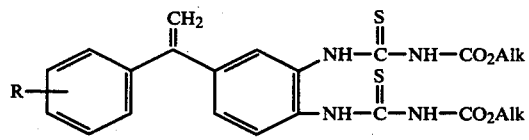

in which:

R is hydrogen, halo such as fluoro, chloro or bromo, $C_{1-4}$-alkoxy, $C_{1-4}$-alkyl or $C_{1-4}$-alkylthio, and Alk is, each, a branched or straight lower alkyl of 1–6 carbons.

The compounds of this invention are prepared by reacting a 1-(3,4-diaminophenyl)-1-phenylethylene with at least two molar equivalents of an alkoxycarbonylisothiocyanate, prepared from an alkali metal thiocyanate and a lower alkyl chloroformate, in an inert organic solvent, such as acetone, at a temperature of the range from room to reflux temperature until the reaction is complete. The desired product is isolated by standard chemical procedures.

The 1,1-diphenylethylene compounds of this invention were evaluated using the method of testing described by V. J. Theodorides, "Anthelmintics: From Laboratory Animals to the Target Species," Chapter 5, Chemotherapy of Infectious Diseases, H. H. Gadebusch, Ed, C.R.C. Press, 1976.

For example, 1-(3,4-bis-(3-(methoxycarbonyl)-2-thioureido)phenyl)-1-phenylethylene, at 5 mg./kg. intraruminally administered to sheep, reduced *Fasciola hepatica* 96.9% compared with infected control animals.

The 1-(3,4-bis-(3-(lower alkoxycarbonyl)-2-thioureido)phenyl)-1-phenylethylenes of formula I have useful general anthelmintic properties, that is, a broad spectrum of activity against parasites of warm-blooded animals. In particular, these compounds have high activity against various helmintic infections of the intestinal tract of mammalian hosts, coupled with low systemic toxicity to the host. Such hosts include man, horses, swine, sheep, dogs, goats, cats and cattle. The activity is observed against nematodes, cestodes and flukes.

For example, the disclosed compounds are generally effective in clearing mice of worm infections for laboratory purposes, among others: *Syphacia obvelata* and *Aspicularis tetraptera* (mouse pinworm), *Nematospiroides dubius* (mouse hookworm), and the migratory stages of *Ascaris suum*.

Other susceptible helminths include *Toxocara canis*, found in naturally infested dogs. Also, parasitic to this host are *Ancylostoma canium, Trichuris vulpis* (whipworm), and *Physalaptera* spp.

These compounds are efficacious against parasites of pigs, such as the migratory stages of *Ascaris suum*, thus preventing the development of verminous pneumonia.

Compounds of Formula I are most efficacious against parasitic gastroenteritis in sheep, such as *Haemonchus contortus*, *Ostertagia* spp., *Trichostrongylus* spp., *Nematodirus* spp., *Trichuris ovis*, *Cooperia* spp., *Strongyloides papillosus, Bunostomum trigoncephalum* and *Oesophagostomum* spp.

Animals of low weight are treated with unit doses ranging no higher than a few milligrams; whereas animals of high body weight, such as ruminants, require proportionately large unit doses ranging up to one or more grams daily. Preferably, a single oral dose selected from the range of 1–10 mg./kg. is administered daily to each animal based on the general body weight of that species.

In nematode infections in sheep, about 2–10 mg./kg. will clear substantially all the worms from the intestinal tract. Essentially, the compounds of formula I have the same spectrum as does the prior art compound, parbendazole, and have a low cost of chemical.

In practice, an active compound of the structure of formula I is usually formulated with a non-toxic carrier therefor to give an anthelmintic composition of this invention. The carrier may be an orally ingestible container for the active ingredient, for example, a pill or a gelatin capsule; or it may be a pharmaceutically acceptable diluent or excipient of the kind normally used in the production of medicaments, for example, maize, starch, terra alba, lactose, sucrose, calcium phosphate, gelatin, talcum, stearic acid, magnesium stearate, dextrin, agar, pectin or acacia.

Exemplary of liquid carriers are peanut oil, olive oil, sesame oil and water. Similarly, the carrier or diluent may include a time delay or continuous release matrix material such as glyceryl monostearate or glyceryl distearate, alone or admixed with a wax.

The compositions are made up in a dosage unit form adapted for the desired mode of administration. Thus, for the preferred oral administration, the dosage unit may take the form of a suspension, tablet, packaged powder, bolus or encapsulated powder. The quantity of active ingredient in each dosage unit will be such that one or more units can be used for each therapeutic administration.

As previously mentioned, the compounds of formula I have general anthelmintic activity and are used for treating or preventing helmintic infections in an animal or human host. They are administered, usually orally, to the host in a nontoxic, but effective, quantity in the form of a pharmaceutical or veterinary composition as herein described. The daily dose range commonly used is selected from the range of about 1 mg./kg. to about 25 mg./kg., preferably about 5 mg./kg.–15 mg./kg., depending on the infection, the species of host and regimen described. One oral dose per day is preferred. The daily dose range is, therefore, often identical to the dosage unit range. In this disclosure, mg./kg. is used to indicate weight of active ingredient per each kilogram of body weight of the infected or potentially infected subject.

The following examples are intended to illustrate the preparation and use of the compounds of this invention. All degrees are Centigrade unless expressed otherwise.

EXAMPLE 1

Sodium hydride (2.4 g., 0.1 mole) was suspended in dimethyl sulfoxide (50 ml.) and heated at 70° under nitrogen until evolution of hydrogen gas ceased (approximately ½ hour). To this suspension at room temperature was added a solution of (methyl)triphenyl phosphonium bromide (35.7 g., 0.1 mole) in dimethyl sulfoxide (100 ml.). The greenish cloudy solution was stirred at ambient temperature for fifteen minutes. To this was added (4-amino-3-nitrophenyl)phenylmethanone (12.1 g., 0.05 mole). The resulting dark red solution was heated at 90° for 18 hours under nitrogen. The reaction mixture was cooled and diluted with water (500 ml.). The pH was adjusted to 7.0 by the addition of 3 N hydrochloric acid. This solution was extracted with ethyl ether (2×150 ml.). The combined organic extracts were washed with water (500 ml.), dried over sodium sulfate and evaporated to dryness. The resulting dark oil was chromatographed over silica gel yielding an orange solid; 1-(4-amino-3-nitrophenyl)-1-phenylethylene, 7.7 g., 64% yield, m.p. 136.7°.

1-(4-Amino-3-nitrophenyl)-1-phenylethylene (7.7 g., 0.032 mole) was dissolved in refluxing ethanol (450 ml.). To this was added, dropwise, a solution of sodium sulfhydrate (38.5 g., 0.45 mole) in water (110 ml.). The resulting solution was refluxed overnight. The reaction mixture was diluted with water (1 l.), cooled and filtered yielding 1-(3,4-diaminophenyl)-1-phenylethylene: 5.6 g., 83% yield, m.p. 109°–110°.

Potassium thiocyanate (10.0 g., 0.104 mole) was dissolved in acetone (250 ml.). Methyl chloroformate (10.0 g., 0.104 mole) was added and the solution was heated at reflux for ½ hour. After the potassium chloride had been removed by filtration, 10.5 g. (0.5 mole) of 1-(3,4-diaminophenyl)-1-phenylethylene was added. The resulting solution was stirred overnight at room temperature. Additional potassium chloride was filtered off and the filtrate concentrated to give a tan solid. The solid residue was recrystallized from acetonitrile (300 ml.)/water (200 ml.) to give 1-(3,4-bis-(3-(methoxycarbonyl)-2-thioureido)phenyl)-1-phenylethylene (7.4 g., 64% yield) m.p. 182°–184°.

Anal. Calcd. C, 54.04; H, 4.53; N, 12.60. Found: C, 53.82; H, 4.64; N, 12.51.

Using isopropyl chloroformate in the above procedure instead of methyl chloroformate gives 1-(3,4-bis-(3-(isopropoxycarbonyl)-2-thioureido)phenyl)-1-phenylethylene. Using pentyl chloroformate gives 1-(3,4-bis-(3-(pentoxycarbonyl)-2-thioureido)phenyl-1-phenylethylene.

Using 1-(3,4-diaminophenyl)-1-(3-methylphenyl)ethylene, 1-(3,4-diaminophenyl-1-(4-methoxyphenyl)ethylene, 1-(3,4-diaminophenyl)-1-(4-fluorophenyl)ethylene or 1-(3,4-diaminophenyl)-1-(2-chlorophenyl)ethylene, all prepared as described above for the unsubstituted compound, gives 1-(3,4-bis-(3-methoxycarbonyl)-2-thioureido)phenyl)-1-(3-methylphenyl)ethylene, 1-(3,4-bis-(3-(methoxycarbonyl)-2-thioureido)phenyl)-1-(4-methoxyphenyl)ethylene, 1-(3,4-bis-(3-(ethoxycarbonyl)-2-thioureido)phenyl)-1-(4-fluorophenyl)ethylene or 1-(3,4-bis-(3-(methoxycarbonyl)-2-thioureido)phenyl)-1-(2-chlorophenyl)ethylene.

EXAMPLE 2

| Typical Cattle Bolus | |
|---|---|
| 1-(3,4-Bis-(3-(methoxycarbonyl)-2-thioureido)phenyl)-1-phenylethylene | 0.04 grams |
| Calcium Phosphate | 2.5 grams |
| Maize Starch | 0.54 grams |
| Talcum | 0.14 grams |
| Gum Arabic | 0.15 grams |
| Magnesium Stearate | 0.5 grams |

The calcium phosphate and the anthelmintic compound are thoroughly mixed, and the mixture reduced to a particle size finer than 60 mesh. About one-half of the starch is added, as an aqueous paste, and the resulting mixture granulated. The granules are passed through a 10 mesh screen and dried at 110°–130° F. for about eight hours. The dried materials are then passed through a No. 16 mesh screen. The guar gum and the balance of the starch are added and the mixture thoroughly blended. Finally, the remainder of the ingredients are added and the entire mass thoroughly mixed and compressed into a bolus. The magnesium stearate, talcum and gum acacia are of a particle size to pass a No. 10 mesh screen.

EXAMPLE 3

| Sheep Drench | Parts by Weight |
|---|---|
| 1-(3,4-Bis-(3-(methoxycarbonyl)-2-thioureido)phenyl-1-phenylethylene | 30 |
| Terra Alba English | 55.5 |
| Tragacanth, U.S.P. | 3.0 |
| Sodium Lauryl Sulfate | 1.5 |
| Water | |

The above solid components are thoroughly mixed, giving a water dispersible powder. This powder can be directly admixed with water in concentration on the order of 10.5 g. of powder to 5 cc. of water.

What is claimed is:

1. A chemical compound of the formula:

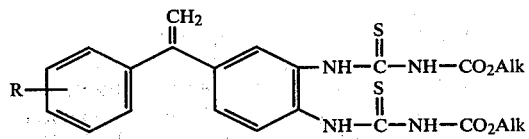

in which:
R is hydrogen, halo, $C_{1-4}$-lower alkoxy, $C_{1-4}$-lower alkyl or $C_{1-4}$-lower alkylthio, and
Alk is, each, $C_{1-6}$-lower alkyl.

2. The compound of claim 1 in which Alk is methyl.

3. The compound of claim 1 being 1-(3,4-bis-(3-(methoxycarbonyl)-2-thioureido)phenyl)-1-phenylethylene.

4. An anthelmintic composition comprising an anthelmintic, nontoxic quantity of a compound of the formula:

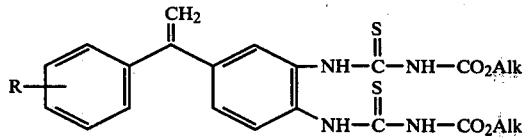

in which:
R is hydrogen, halo, $C_{1-4}$-lower alkoxy, $C_{1-4}$-lower alkyl or $C_{1-4}$-lower alkylthio, and
Alk is $C_{1-6}$-lower alkyl, combined with a pharmaceutical or veterinary carrier therefor.

5. The composition of claim 4 in which the compound is 1-(3,4-bis-(3-(methoxycarbonyl)-2-thioureido)phenyl)-1-phenylethylene.

6. The composition of claim 4 in which the quantity of compound is selected from the range of 5–15 mg./kg.

7. The composition of claim 5 in which the quantity of compound is selected from the range of 5–15 mg./kg.

8. A method of inducing anthelmintic activity curatively or prophylactically in an animal subject comprising administering orally to said animal a nontoxic, anthelmintic quantity of a compound of the formula:

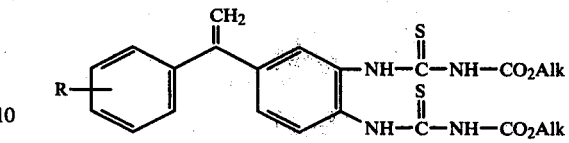

in which:
R is hydrogen, halo, $C_{1-4}$-lower alkoxy, $C_{1-4}$-lower alkyl or $C_{1-4}$-lower alkylthio, and
Alk is $C_{1-6}$-lower alkyl, combined with a pharmaceutical or veterinary carrier therefor.

9. The method of claim 8 in which the compound is 1-(3,4-bis-(3-(methoxycarbonyl)-2-thioureido)phenyl)-1-phenylethylene.

10. The method of claim 8 in which the quantity is selected from the range of 5–15 mg./kg. and is administered once daily.

11. The method of claim 9 in which the quantity is selected from the range of 5–15 mg./kg. administered once daily.

* * * * *